United States Patent [19]

Shankar et al.

[11] Patent Number: 5,455,222

[45] Date of Patent: Oct. 3, 1995

[54] 1-SUBSTITUTED-5-THIOMETHYL-THIOCYANATO-1H-TETRAZOLES, COMPOSITIONS CONTAINING THEM AND THEIR USE AS ANTIMICROBIAL AND MARINE ANTIFOULING AGENTS

[75] Inventors: Ravi B. Shankar; Duane R. Romer; R. Garth Pews, all of Midland, Mich.

[73] Assignee: The Dow Chemical Company, Midland, Mich.

[21] Appl. No.: 360,491

[22] Filed: Dec. 21, 1994

[51] Int. Cl.$^6$ .................... C07D 257/04; A61K 31/41
[52] U.S. Cl. .................... 504/156; 548/251; 514/381
[58] Field of Search ............. 548/251; 514/381; 504/156

[56] References Cited

U.S. PATENT DOCUMENTS 4,110,338  8/1978  Kamiya et al. ............... 548/251
5,177,092  1/1993  Remy et al. ............... 548/251

Primary Examiner—Joseph K. McKane

[57] ABSTRACT

Disclosed are substituted-5-thiomethylthiocyanato-1H-tetrazole compounds corresponding to the formula

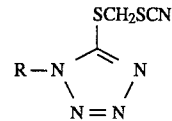

wherein R represents a $C_1$–$C_6$ straight or branched chain alkyl radical, a $C_3$–$C_6$ cycloalkyl or a phenyl radical of the formula

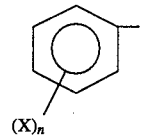

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is 0–5.

These compounds have been found to exhibit antimicrobial and marine antifouling activity in industrial and commercial applications and compositions containing these compounds are so employed.

25 Claims, No Drawings

1-SUBSTITUTED-5-THIOMETHYL-THIOCYANATO-1H-TETRAZOLES, COMPOSITIONS CONTAINING THEM AND THEIR USE AS ANTIMICROBIAL AND MARINE ANTIFOULING AGENTS

FIELD OF THE INVENTION

The present invention is directed to novel 1-substituted-5-thiomethylthiocyanato-1H-tetrazole compounds, compositions containing said compounds and the use of these compositions as antimicrobial and marine antifouling agents.

SUMMARY OF THE INVENTION

The present invention is directed to compounds corresponding to the formula

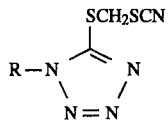

wherein R represents a $C_1$–$C_6$ straight or branched chain alkyl radical, a $C_3$–$C_6$ cycloalkyl or a phenyl radical of the formula

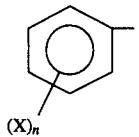

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is an integer of from 0–5.

The present invention is also directed to antimicrobial compositions comprising an inert diluent and an antimicrobially-effective amount of a compound corresponding to Formula 1.

The present invention is further directed to a method for inhibiting microorganisms in a microbial habitat comprising contacting said microbial habitat with an antimicrobially-effective amount of a compound corresponding to Formula 1.

The antimicrobial compositions of the present invention can also be employed to treat surfaces exposed to a marine environment in which marine organisms grow to prevent the growth of said marine organisms on said surfaces.

The preferred compounds of the present invention include those wherein R represents phenyl, 3- or 4-chlorophenyl, 3-methylphenyl and cyclohexyl, and most preferably cyclohexyl.

DETAILED DESCRIPTION OF THE INVENTION

In the present specification and claims, the term "alkali metal" is employed to designate sodium, potassium, lithium or cesium.

In the present specification and claims, the term "halo" is employed to designate bromo, chloro, fluoro or iodo.

In the following process schematic formulas, certain specific alkali metals, halo groups, specific solvents and the like are set forth. These representations are only presented for convenience and are not to be considered as an indication that these specifically representations are the only groups or materials which can be employed.

The 1-substituted-5-thiomethylthiocyanato-1H-tetrazole compounds of the present invention can be prepared utilizing a number of procedures. In one such procedure, an appropriate 1-substituted-5-mercapto-1H-tetrazole compound is reacted with an alkali metal methoxide to prepare the corresponding alkali metal salt product. The general scheme for this first reaction step is as follows:

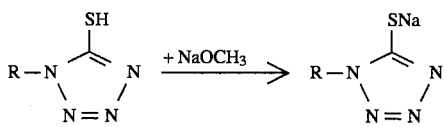

wherein R is as hereinabove defined.

In carrying out the first reaction step, the appropriate 5-mercapto-1H-tetrazole compound is dissolved in an alkanol solvent such as methanol containing an excess (about 1.0–1.5 equivalents) of an alkali metal alkoxide such as sodium methoxide and the mixture is stirred at room temperature for about 15 minutes to about an hour. The reaction mixture is then concentrated under reduced pressure and the residue dissolved in an inert solvent such as dimethylformamide, tetrahydroformamide or glyme.

The desired 1-substituted-5-thiomethylthiocyanato-1H-tetrazole product is then reacted with an excess (about 1.0–2.0 equivalents) of a halomethyl (or ethyl)thiocyanate, such as chloromethylthiocyanate or chloroethylthiocyanate. The general scheme for this first reaction step is as follows:

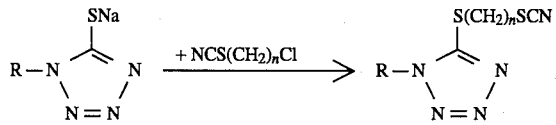

wherein R is as hereinabove defined.

In another procedure, a solution of 1-substituted-5-((chloromethyl)thio)-1H-tetrazole and an alkali metal thiocyanate such as potassium thiocyanate in a solvent such as dimethylformamide are heated at a temperature of from about 50 to about 100° C. for from about 6 to about 24 hours. The reaction mixture is cooled to room temperature and diluted with water. This mixture is extracted with a solvent such as methylene chloride and the thus obtained organic layers are washed with water, then with brine and then dried. After concentration, the product which forms can be further purified by conventional techniques such as chromatography over silica gel using hexane/ethyl acetate as the eluent. The general scheme for this reaction step is as follows:

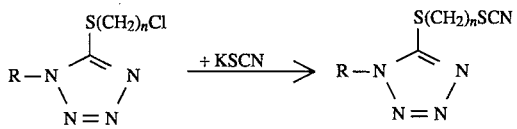

wherein R is as hereinabove defined.

The following examples illustrate the present invention and the manner by which it can be practiced but, as such, should not be construed as limitations upon the overall scope of the same.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an excess of one reactant, the use of a catalyst, the use of high temperature and/or high pressure equipment, high speed mixing and other such conventional changes are within the scope of the present invention.

The desired product can be separated from the reaction product of the above preparative procedures employing conventional separatory procedures known to those skilled in the art including steps of solvent extraction, filtration, water washing, column chromatography, neutralization, acidification, crystallization and distillation.

The structure identity of all compounds is confirmed by proton nuclear magnetic resonance spectroscopy ($^1$H NMR), recorded at 300 MHz ; carbon nuclear magnetic resonance spectroscopy ($^{13}$C NMR) recorded at 75 MHz; infrared spectroscopy (IR) and gas chromatography/mass spectrometry (GC/MS). All of the reactions are conducted under a positive pressure of nitrogen.

EXAMPLE I

Preparation of 1-Phenyl-5-thiomethylthiocyanato-1H-tetrazole

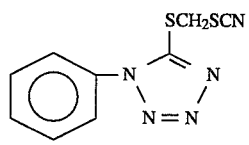

A solution of 1.0 gram(g)(0.0044 mole) of 5-((chloromethyl)thio)-1-phenyl-1H-tetrazole and 0.86 g (0.0088 mole) of potassium thiocyanate in 15 mL of dimethylformamide was heated at 65° C. for 24 hours. The reaction mixture was cooled to room temperature and slowly poured, with stirring, into 100 mL of water. The resulting suspension was extracted twice with 50 mL portions of methylene chloride, and the combined organic layers were washed first with water and then with brine and then dried over sodium sulfate. The material thus obtained was concentrated to give the crude product as a solid which was purified by flash chromatography eluting with 50 percent hexanes/ethyl acetate giving the above-named product as a yellow solid (0.93 g, 85 percent of theoretical). $^1$H NMR (300 MHz, CDCl$_3$) δ 7.58 (bs, 5H), 4.92 (s, 2H); $^{13}$C NMR (75 MHz, CDCl$_3$) δ 151.30, 132.59, 130.47, 129.88, 123.38, 110.73, 37.54.

EXAMPLE II

Preparation of 1-(3-Chlorophenyl)- 5-thiomethylthiocyanato-1H-tetrazole

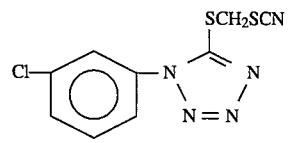

This compound was prepared following the preparative procedures of Example I. The product was recovered as a white solid melting at 138°–140° C., in a yield of 66 percent of theoretical. $^1$H NMR (300 MHz, CDCl$_3$) δ 4.95 (s, 2H), 7.56 (m, 4H); $^{13}$C NMR (75 MHz, CDCl$_3$) δ 37.65, 110.61, 121.47, 121.47, 123.69, 130.69, 131.02, 133.56, 135.65, 151.44.

EXAMPLE III

Preparation of 1-(4-Chlorophenyl)-5-thiomethylthiocyanato-1H-tetrazole

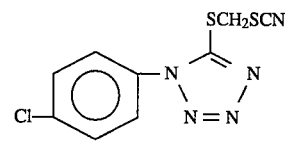

This compound was prepared following the preparative procedures of Example I. The product was recovered as a white solid in a yield of 67 percent of theoretical. $^1$H NMR (300 MHz, CDCl$_3$) δ 4.93 (s, 2H), 7.55 (m, 4H); $^{13}$C NMR (75 MHz, CDCl$_3$) δ 37.51, 110.54, 124.71, 130.00, 131.00, 136.35, 151.37.

EXAMPLE IV

Preparation of 1-(4-Bromophenyl)-5-thiomethylthiocyanato-1H-tetrazole

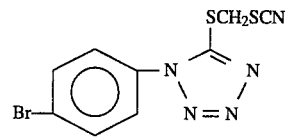

This compound was prepared following the preparative procedures of Example I. The product was recovered as a white solid which melted at 98°–100° C. in a yield of 65 percent of theoretical. $^1$H NMR (300 MHz, CDCl$_3$) δ 4.92 (s, 2H), 7.48 (d, J=8.8 Hz, 2H), 7.74 (d, J=8.8 Hz, 2H); $^{13}$C NMR (75 MHz, CDCl$_3$) δ 37.68, 110.63, 124.75, 124.98, 131.70, 131.24, 151.35.

EXAMPLE V

Preparation of 1-(4-Fluorophenyl)-5-thiomethylthiocyanato-1H-tetrazole

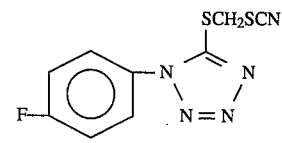

This compound was prepared following the preparative procedures of Example I. The product was recovered as an oil in a yield of 60 percent of theoretical. $^1$H NMR (300 MHz, CDCl$_3$) δ 4.95 (s, 2H), 7.31 (m, 2H), 7.60 (m, 2H); $^{13}$C NMR (75 MHz , CDCl$_3$) δ 37.49, 110.56, 116.81, 117.26, 125.76, 125.88, 128.55, 128.59, 151.53, 161.35, 164.70.

EXAMPLE VI

Preparation of 1-(3-Methylphenyl)-5-thiomethylthiocyanato-1H-tetrazole

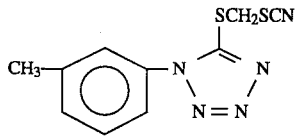

This compound was prepared following the preparative procedures of Example I. The product was recovered as a white solid melting at 68°–70° C., in a yield of 70 percent of theoretical. $^{1}$H NMR (300 MHz, CDCl$_{3}$) δ 2.45 (s, 3H), 4.93 (s, 2H), 7.35–7.46 (m, 4H); $^{13}$C NMR (75 MHz, CDCl$_{3}$) δ 20.94, 37.46, 110.64, 120.25, 123.84, 129.48, 131.10, 132.43, 140.23, 151.20.

EXAMPLE VII

Preparation of 1-(4-Methylphenyl)-5-thiomethylthiocyanato-1H-tetrazole

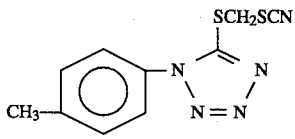

This compound was prepared following the preparative procedures of Example I. The product was recovered as a white solid in a yield of 62 percent of theoretical. $^{1}$H NMR (300 MHz, CDCl$_{3}$) δ 2.47 (s, 3H), 4.87 (s, 2H), 7.35–7.46 (m, 4H); $^{13}$C NMR (75 MHz, CDCl$_{3}$) δ 21.24, 37.70, 110.84, 120.25, 123.40, 130.26, 130.55, 141.16, 151.31.

EXAMPLE VIII

Preparation of 1-(4-Methoxyphenyl)-5-thiomethylthiocyanato-1 H-tetrazole

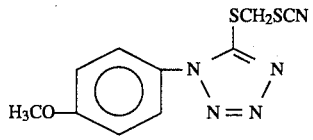

This compound was prepared following the preparative procedures of Example I. The product was recovered as a white solid melting at 112° C. in a yield of 70 percent of theoretical. $^{1}$H NMR (300 MHz, CDCl$_{3}$) δ 3.87 (s, 3H), 5.13 (s, 2H), 7.21 (d, J=9.1 Hz, 2H), 7.61 (d, J=9.1 Hz, 2H); $^{13}$C NMR (75 MHz, CDCl$_{3}$) δ 37.77, 55.71, 111.87, 115.12, 125.31, 126.45, 152.36, 160.80.

EXAMPLE IX

Preparation of 1-(tertiary-Butylphenyl)-5-thiomethylthiocyanato-1H-tetrazole

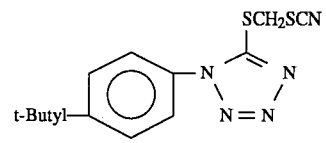

This compound was prepared following the preparative procedures of Example I. The product was recovered as a white solid melting at 80°–82° C. in a yield of 68 percent of theoretical. $^{1}$H NMR (300 MHz, CDCl$_{3}$) δ 1.75 (s , 9H), 4.89 (s, 2H); $^{13}$C NMR (75 MHz , CDCl$_{3}$) δ 28.89, 38.36, 61.71, 111.19, 149.49.

EXAMPLE X

Preparation of 1-(Cyclohexyl)-5-thiomethylthiocyanato-1H-tetrazole

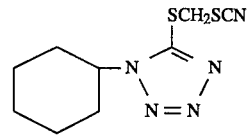

This compound was prepared following the preparative procedures of Example I. The product was recovered as a yellow solid melting at 58°–60° C., in a yield of 80 percent of theoretical. $^{1}$H NMR (300 MHz, CDCl$_{3}$) δ 1.2–1.6 (m, 3H), 1.7–2.2 (m, 7H), 4.2 (m, 1H), 4.93 (s, 2H); $^{13}$C NMR (75 MHz, CDCl$_{3}$) δ 24.33, 24.62, 31.73, 37.62, 58.40, 110.56, 149.56.

EXAMPLE XI

Preparation of 1-(4-Nitrophenyl)-5-thiomethylthiocyanato-1H-tetrazole

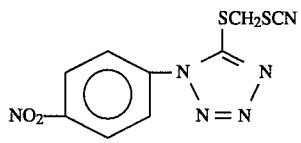

To a suspension of 0.8 g (0.01 mole) of sodium azide in 50 mL of methanol, at room temperature, was added 1.8 g (0.0 mole) of 4-nitrophenyl isothiocyanate and the mixture was allowed to stir for 2 hours. The solvent was evaporated off and the residue was dissolved in water and acidified. The precipitate which formed was filtered off, dried over sodium sulfate and dissolved in methanol containing 1 equivalent of sodium methoxide and stirred for 30 minutes. The solvent was evaporated off and the residue was dissolved in 20 mL of dimethylformamide and 1.62 g (0.015 mole) of chloromethyl thiocyanate was added and the mixture was allowed to stir overnight (about 16 hours). The reaction mixture was diluted methylene chloride, washed with water and concentrated to dryness under reduced pressure. The residue was chromatographed over silica gel with 3:1 hexane/ethyl acetate as eluent to yield the 1-(4-Nitrophenyl)-5-thiomethylthiocyanato-1H-tetrazole as a yellow oil in an amount of 1.32 g (45 percent of theoretical). $^1$H NMR (300 MHz, CDCl$_3$) δ 4.95 (s 2H), 7.88 (d, J=8.7 Hz, 2H), 8.50 (d, J=9 Hz, 2H); $^{13}$C NMR (75 MHz, CDCl$_3$) δ 37.91, 110.43, 124.11, 125.65, 137.61, 148.35, 151.60.

EXAMPLE XII

Preparation of 1-(4-Cyanophenyl)-5-thiomethylthiocyanato-1H-tetrazole

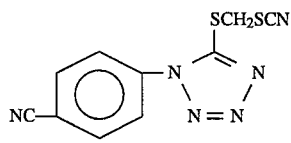

A solution of 3.0 g (0.019 mole) of 4-cyanophenyl isothiocyanate and 1.46 g (0.023 mole) of sodium azide in 100 mL of ethanol was heated to 70° C. and the mixture was allowed to stir for an hour. The reaction mixture was cooled, filtered and the solvent was evaporated off. The residue was slurried in methanol containing 1.1 equivalents of sodium methoxide and was stirred for 30 minutes. The solvent was evaporated off and the residue was dissolved in 10 mL of dimethylformamide and 3.0 g (0.028 mole) of chloromethyl thiocyanate was added and the mixture was allowed to stir overnight (about 16 hours). The reaction mixture was diluted methylene chloride, washed with water and concentrated to dryness under reduced pressure. The residue was chromatographed over silica gel with 3:1 hexane/ethyl acetate as eluent to yield the 1-(4-Cyanophenyl)-5-thiomethylthiocyanato-1H-tetrazole in an amount of 1.67 g (32 percent of theoretical) as a yellowish white solid which melted at 114°–116° C. $^1$H NMR (300 MHz, CDCl$_3$) δ 4.95 (s, 2H), 7.82 (d, J=8.6 Hz, 2H), 7.96 (d, J=8.6 Hz, 2H); $^{13}$C NMR (75 MHz, CDCl$_3$) δ 37.81, 110.51, 114.41, 117.03, 123.90, 134.09, 136.17, 151.51.

Antimicrobial Activity

The compounds of this invention are useful as antimicrobial additives, and they can be added to industrial products such as paints, inks adhesives, soaps, cutting oils, textiles paper pigment slurries and styrene-butadiene latexes used for paper coatings to provide needed antimicrobial properties. The compounds are also used as antimicrobial additives in such personal care products as hand creams, lotions, shampoos and hand soaps. A further advantage in the use of the compounds of this invention is their cost-effectiveness for applications which need to have an antimicrobial continuously replenished, such as in cooling towers and pulp and paper mills.

As appreciated by those skilled in the art, each of the compounds disclosed herein are not necessarily active at the same concentrations or against he same microbial species. There may be some compound-to-compound variation in antimicrobial potency and spectrum of antimicrobial activity.

The antimicrobial compounds of the present invention may be added to formulations susceptible to microbial growth. They may be added either undiluted or dissolved in inert diluents such as organic solvents such as glycols, alcohols or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular compound tested and microorganism treated. Additionally, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "habitat" refers to a place or site where a microorganism naturally or normally lives or grows. Typically, such a habitat will be an area that provides a moisture source, nutrient source, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

TABLE I

Identification of Compounds Used in Antimicrobial Activity Tests

| Compound Example No. | Chemical Identity |
|---|---|
| I | 1-Phenyl-5-thiomethyl-thiocyanato-1H-tetrazole |
| II | 1-(3-Chlorophenyl)-5-thiomethylthiocyanato-1H-tetrazole |
| III | 1-(4-Chlorophenyl)-5-thiomethylthiocyanato-1H-tetrazole |
| IV | 1-(4-Bromophenyl)-5-thiomethylthiocyanato-1H-tetrazole |
| V | 1-(4-Fluorophenyl)-5-thiomethylthiocyanato-1H-tetrazole |
| VI | 1-(3-Methylphenyl)-5-thiomethylthiocyanato-1H-tetrazole |
| VII | 1-(4-Methylphenyl)-5-thiomethylthiocyanato-1H-tetrazole |
| VIII | 1-(4-Methoxyphenyl)-5-thiomethylthiocyanato-1H-tetrazole |
| IX | 1-(tertiary-Butylphenyl)-5-thiomethylthiocyanato-1H-tetrazole |
| X | 1-(Cyclohexyl)-5-thiomethylthiocyanato-1H-tetrazole |
| XI | 1-(4-Nitrophenyl)-5-thiomethylthiocyanato-1H-tetrazole |
| XII | 1-(4-Cyanophenyl)-5-thiomethylthiocyanato-1H-tetrazole |

The minimum inhibitory concentration (MIC) for the compounds listed in Table I is determined for 9 bacteria, using nutrient agar, and 7 yeast and fungi, using malt yeast agar. A one percent solution of the test compound is prepared in a mixture of acetone and water.

Nutrient agar is prepared at pH 6.8, representing a neutral medium, and at pH 8.2, representing an alkaline medium. The nutrient agars are prepared by adding 23 g of nutrient agar to one liter of deionized water. In addition, the alkaline medium is prepared by adjusting a 0.04M solution of N-[tris-(hydroxymethyl)methyl]glycine buffered deionized water with concentrated sodium hydroxide to a pH of 8.5.

Malt yeast agar is prepared by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension to 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC test described above along with their respective American Type Culture Collection (ATCC) identification numbers.

TABLE II

Organisms Used in the Minimum Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables III and IV, the MIC values of the compounds described in Table I as compared to the MIC of a standard commercial preservative (with 1-(3-chloroallyl)-3,5,7-triaza-1-azoniaadamantane chloride as the active agent and referred to in Tables III and IV as "STANDARD I") are set forth for the bacteria organisms and yeast/fungi organisms which are listed in Table II.

TABLE III

Minimum Inhibitory Concentrations for Test Compounds in Bacteria Species (in ppm)

| Compound | ORGANISMS | | | | | | | | |
|---|---|---|---|---|---|---|---|---|---|
| | Bs | Ea | Ec | Kp | Pv | PRD | Pa | Sc | Sa |
| STANDARD | | | | | | | | | |
| PH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| (I) | | | | | | | | | |
| pH 6.8 | <10 | 250 | 50 | 100 | 25 | 250 | 100 | 100 | 25 |
| pH 8.2 | 50 | 500 | 250 | 100 | 100 | 250 | 100 | 250 | 50 |
| (II) | | | | | | | | | |
| pH 6.8 | 100 | 500 | 500 | 250 | 100 | 500 | 500 | 500 | 250 |

TABLE III-continued

Minimum Inhibitory Concentrations for Test Compounds in Bacteria Species (in ppm)

| Compound | Bs | Ea | Ec | Kp | Pv | PRD | Pa | Sc | Sa |
|---|---|---|---|---|---|---|---|---|---|
| pH 8.2 (III) | 250 | 500 | 500 | 250 | 250 | 250 | 500 | 500 | 100 |
| pH 6.8 | <10 | 25 | 25 | 25 | 25 | 25 | 25 | 25 | 25 |
| pH 8.2 (IV) | 50 | 250 | 250 | 50 | 100 | 50 | 25 | 100 | 50 |
| pH 6.8 | <10 | 500 | 500 | 500 | 500 | 500 | 500 | 500 | 500 |
| pH 8.2 (V) | 25 | 500 | 500 | 500 | 500 | 500 | 500 | 500 | 500 |
| pH 6.8 | <10 | 250 | 100 | 100 | 50 | 50 | 50 | 100 | 25 |
| pH 8.2 (VI) | 50 | 500 | 500 | 250 | 250 | 100 | 100 | 250 | 50 |
| pH 6.8 | <10 | 500 | 500 | 250 | 100 | 500 | 500 | 500 | 25 |
| pH 8.2 (VII) | 25 | 500 | 500 | 100 | 100 | 500 | 250 | 500 | 50 |
| pH 6.8 | <10 | >500 | 500 | 250 | 100 | 500 | 500 | >500 | 25 |
| pH 8.2 (VIII) | <10 | >500 | 500 | 100 | 250 | 250 | 250 | >500 | 50 |
| pH 6.8 | <10 | 250 | 100 | 250 | 250 | 100 | 100 | 250 | 25 |
| pH 8.2 (IX) | 25 | 500 | 500 | 100 | 500 | 500 | 100 | 500 | 100 |
| pH 6.8 | 25 | 500 | 50 | 250 | 250 | 500 | 500 | 50 | 50 |
| pH 8.2 (X) | 50 | 500 | 250 | 100 | 100 | 500 | 500 | 100 | 50 |
| pH 6.8 | <10 | 500 | 250 | 250 | 250 | 500 | 250 | 250 | 25 |
| pH 8.2 (XI) | 25 | 500 | 500 | 100 | 250 | 500 | 250 | 500 | 50 |
| pH 6.8 | >100 | >100 | >100 | <100 | <100 | >100 | >100 | >100 | 100 |
| pH 8.2 (XII) | >100 | >100 | >100 | >100 | >100 | >100 | >100 | >100 | 50 |
| pH 6.8 | <10 | 500 | 200 | 100 | 100 | 500 | 500 | 500 | 20 |
| pH 8.2 | 40 | >400 | 400 | 100 | 200 | 400 | 200 | 400 | 100 |

TABLE IV

Minimum Inhibitory Concentrations for Test Compounds in Yeast/Fungi Species (in ppm)

| COMPOUND | An | Ca | PC | SC | Tv | Ap | Fo |
|---|---|---|---|---|---|---|---|
| STANDARD | >500 | >500 | >500 | 500 | >500 | >500 | >500 |
| I | 5 | 25 | 2.5 | 5 | 25 | 2.5 | 10 |
| II | <10 | <10 | <10 | <10 | 25 | <10 | <10 |
| III | <1 | 5 | <1 | 2.5 | 5 | 2.5 | 2.5 |
| IV | <10 | 25 | <10 | <10 | 25 | <10 | <10 |
| V | 5 | 25 | 2.5 | 5 | 25 | 2.5 | 5 |
| VI | 5 | 5 | <1 | <1 | 25 | <1 | <1 |
| VII | 2.5 | 10 | <1 | <1 | 10 | <1 | 5 |
| VIII | <10 | 25 | <10 | <10 | 25 | <10 | <10 |
| IX | 5 | 100 | 2.5 | 10 | 100 | 2.5 | 25 |
| X | 5 | 50 | <1 | 5 | 50 | <1 | 5 |
| XI | 5 | 100 | <2.5 | 10 | 25 | 10 | 25 |
| XII | <10 | 200 | <10 | 40 | 40 | <10 | 20 |

Marine Antifouling Activity

The present invention is also directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a marine antifouling effective amount of the compound of this invention.

As appreciated by those skilled in the art, not all of the compounds disclosed herein are active at the same concentrations or against the same marine organism species. That is, there may be some compound-to-compound variation in marine antifouling potency and spectrum of marine antifouling activity. Furthermore, a compound's marine antifouling activity may be dependent on the specific materials with which the compound is formulated to form a marine antifouling composition.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is $0.381 \times 10^{-3}$ m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

A candidate marine antifoulant compound (1.0 g) is stirred into a resinous latex binder (9.0 g). A portion of the compound/binder mixture (1.5 g) is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit from between ten to thirty minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine surfactant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 3 and 6 weeks during which time the control test panels become substantially covered with mature marine organism growth on both the topside and underside exposures.

After being removed from the exposure support apparatus, each test panel is inspected and rated for marine organism growth on both the treated and untreated areas of the test panel. The marine organisms present on the treated and untreated areas are noted. The presence of algae spores and bacterial slime are noted but not included in rating each test panel. The test panels are rated on a scale from 10 (representing completely free of marine organism growth) to 0 (representing completely covered with marine organism growth).

In Table V, the marine antifouling rating values for some of the compounds listed in Table I are set forth, as well as the ratings for control panels (with no marine antifouling compound and referred to in Table V as "Control").

In addition, test panels were prepared using tributyl tin oxide, a known marine antifouling compound. One set of such panels used the tributyl tin oxide in a commercially available ship-hull paint (referred to in Table V as "STANDARD II") which was employed in the same manner as the resinous latex binder used on the other test panels. A second set of such panels used the tributyl tin oxide at a 10 percent concentration in the resinous latex binder (referred to in Table V as "STANDARD III").

TABLE V

Marine Antifouling Rating for Test Compounds

| | Marine Antifouling Ratings | | | |
|---|---|---|---|---|
| | 6 Week Test | | 15 Week Test | |
| Compound Example No. | Top Panel | Bottom Panel | Top Panel | Bottom Panel |
| I | 9 | 9 | — | — |
| II | 9 | 10 | 9 | 6 |
| III | 9 | 9 | 4 | 1 |
| VI | 9 | 10 | 8 | 9 |
| X | 9 | 10 | 4 | 8 |
| Control | 9 | 4 | 2 | 0 |
| STANDARD II | 10 | 10 | 10 | 9 |
| STANDARD III | 9 | 10 | 1 | 1 |

What is claimed is:

1. A compound corresponding to the formula

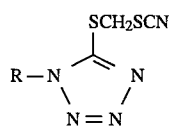

wherein R represents a $C_1$–$C_6$ straight or branched chain alkyl radical, a $C_3$–$C_6$ cycloalkyl or a phenyl radical of the formula

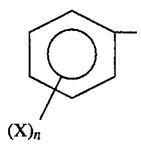

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is 0–5.

2. A compound of claim 1 wherein R represents a $C_1$–$C_6$ straight chain radical, a $C_1$–$C_6$ branched chain alkyl radical or a $C_3$–$C_6$ cycloalkyl radical.

3. The compound of claim 2 which is 1-Cyclohexyl-5-thiomethylthiocyanato-1H-tetrazole.

4. A compound of claim 1 wherein R represents a phenyl radical and X represents hydrogen, halo, a $C_1$–$C_6$ branched chain alkyl radical, a $C_3$–$C_6$ cycloalkyl radical, a $C_1$–$C_6$ straight chain alkoxy radical, cyano or nitro and n is 1.

5. The compound of claim 4 which is 1(3-Chlorophenyl)-5-thiomethylthiocyanato-1H-tetrazole.

6. The compound of claim 4 which is 1-(4-Chlorophenyl)-5-thiomethylthiocyanato-1H-tetrazole.

7. The compound of claim 4 which is 1-(3-Methylphenyl)-5-thiomethylthiocyanato-1H-tetrazole.

8. An antimicrobial composition comprising an inert diluent and an antimicrobially-effective amount of a compound corresponding to the formula

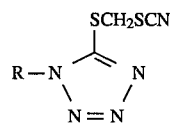

wherein R represents a $C_1$–$C_6$ straight or branched chain alkyl radical, a $C_3$–$C_6$ cycloalkyl or a phenyl radical of the formula

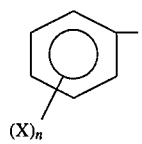

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is 0–5.

9. A composition of claim 8 wherein R represents a $C_1$–$C_6$ straight chain radical, a $C_1$–$C_6$ branched chain alkyl radical or a $C_3$–$C_6$ cycloalkyl radical.

10. The composition of claim 9 which is 1-Cyclohexyl-5-thiomethylthiocyanato-1H-tetrazole.

11. A composition of claim 8 wherein R represents a phenyl radical and X represents hydrogen, halo, a $C_1$–$C_6$ branched chain alkyl radical, a $C_3$–$C_6$ cycloalkyl radical, a $C_1$–$C_6$ straight chain alkoxy radical, cyano or nitro and n is 1.

12. The composition of claim 11 which is 1-(3-Chlorophenyl)-5-thiomethylthiocyanato-1H-tetrazole.

13. The composition of claim 11 which is 1-(4-Chlorophenyl)-5-thiomethylthiocyanato-1H-tetrazole.

14. The composition of claim 11 which is 1-(3-Methylphenyl)-5-thiomethylthiocyanato-1H-tetrazole.

15. A method for inhibiting microorganisms in a microbial habitat comprising contacting said microbial habitat with an antimicrobially-effective amount of a compound corresponding to the formula

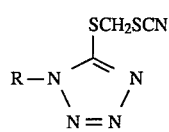

wherein R represents a $C_1$–$C_6$ straight or branched chain alkyl radical, a $C_3$–$C_6$ cycloalkyl or a phenyl radical of the formula

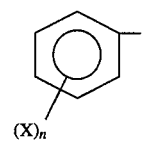

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is 0–5.

16. A method of claim 15 wherein R represents a $C_1$–$C_6$ straight chain radical, a $C_1$–$C_6$ branched chain alkyl radical or a $C_3$–$C_6$ cycloalkyl radical.

17. The method of claim 16 which is 1-Cyclohexyl-5-thiomethylthiocyanato-1H-tetrazole.

18. A method of claim 15 wherein R represents a phenyl radical and X represents hydrogen, halo, a $C_1$–$C_6$ branched chain alkyl radical, a $C_3$–$C_6$ cycloalkyl radical, a $C_1$–$C_6$ straight chain alkoxy radical, cyano or nitro and n is 1.

19. The method of claim 18 which is 1-(3-Chlorophenyl)-5-thiomethylthiocyanato-1H-tetrazole.

20. The method of claim 18 which is 1-(4-Chlorophenyl)-5-thiomethylthiocyanato-1H-tetrazole.

21. The method of claim 18 which is 1-(3-Methylphenyl)-5-thiomethylthiocyanato-1H-tetrazole.

22. The method of claim 15 wherein the compound is present in an amount to provide from about 1 part per million to about 5,000 parts per million by weight of the compound to a microbial habitat that is contacted with the composition.

23. A composition useful in preventing the growth of marine organisms on a surface exposed to a marine environment in which marine organisms grow comprising an inert diluent and a marine antifouling effective amount of a compound corresponding to the formula

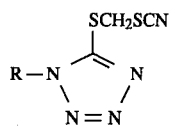

wherein R represents a $C_1$–$C_6$ straight or branched chain alkyl radical, a $C_3$–$C_6$ cycloalkyl or a phenyl radical of the formula

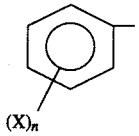

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is 0–5.

24. A method for preventing the growth of marine organisms on a surface exposed to a marine environment in which marine organisms grow comprising contacting said surface with a marine antifouling effective amount of a compound corresponding to the formula

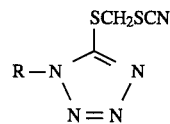

wherein R represents a $C_1$–$C_6$ straight or branched chain alkyl radical, a $C_3$–$C_6$ cycloalkyl or a phenyl radical of the formula

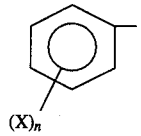

wherein each X independently represents hydrogen, halo, a $C_1$–$C_6$ straight or branched chain alkyl radical, a $C_3$–$C_6$ cycloalkyl radical, a $C_1$–$C_6$ straight or branched chain alkoxy radical, a $C_3$–$C_6$ cycloalkoxy radical, cyano or nitro and n is 0–5.

25. The method of claim 24 wherein the compound is contacted with the surface in an amount from about 1 to about 30 weight percent of a composition comprising an inert diluent and the compound.

* * * * *